United States Patent
Nakajima et al.

(10) Patent No.: US 7,338,480 B2
(45) Date of Patent: Mar. 4, 2008

(54) DIAGNOSIS CATHETER FOR INTERSTITIAL CYSTITIS

(75) Inventors: Yasuhiko Nakajima, Kanagawa (JP); Tomohiro Ueda, Kyoto (JP)

(73) Assignee: Tsukada Medical Research Co., Ltd., Tokyo (JP)

( * ) Notice: Subject to any disclaimer, the term of this patent is extended or adjusted under 35 U.S.C. 154(b) by 0 days.

(21) Appl. No.: 10/492,165

(22) PCT Filed: Nov. 14, 2002

(86) PCT No.: PCT/JP02/11881

§ 371 (c)(1),
(2), (4) Date: Apr. 9, 2004

(87) PCT Pub. No.: WO2004/043260

PCT Pub. Date: May 27, 2004

(65) Prior Publication Data

US 2005/0215981 A1   Sep. 29, 2005

(51) Int. Cl.
*A61M 25/00* (2006.01)
*A61M 99/00* (2006.01)
*A61N 1/00* (2006.01)
*A61B 5/04* (2006.01)

(52) U.S. Cl. .................. 604/509; 604/96.01; 604/544; 604/117; 604/138; 607/138; 600/373; 600/435; 600/585

(58) Field of Classification Search ................. 600/433; 607/122, 138; 604/27, 544, 117, 138, 533, 604/164.01, 509, 96.01
See application file for complete search history.

(56) References Cited

U.S. PATENT DOCUMENTS

| | | | | | |
|---|---|---|---|---|---|
| 3,720,210 | A | * | 3/1973 | Diettrich | 604/533 |
| 5,322,501 | A | * | 6/1994 | Mahmud-Durrani | 604/544 |
| 5,476,434 | A | * | 12/1995 | Kalb et al. | 600/30 |
| 5,964,732 | A | * | 10/1999 | Willard | 604/117 |
| 2001/0020162 | A1 | * | 9/2001 | Mosel et al. | 604/544 |

FOREIGN PATENT DOCUMENTS

| | | |
|---|---|---|
| JP | 9-117453 A | 5/1997 |
| JP | 11-393 A | 1/1999 |
| JP | 11-511040 A | 9/1999 |

* cited by examiner

*Primary Examiner*—Tatyana Zalukaeva
(74) *Attorney, Agent, or Firm*—Sughrue Mion, PLLC

(57) ABSTRACT

A diagnosis catheter 1 for an interstitial cystitis is connected to a current perception threshold inspection apparatus 4. A catheter body 11 is made of a soft flexible material and includes a bladder-dwelling distal end section A and a diagnosis section B adjacent the distal end section A at a proximal end side of the body 11. A core member 12 is made of a hard flexible material and is inserted into the diagnosis section B in the catheter body 11. An inflatable balloon 13 is mounted on an outer periphery around the bladder-dwelling distal end section A of the catheter body 11. A fluid supply passage 16 is provided in the catheter body 11 so that an end of the passage 16 is communicated to the balloon 13 and a proximal end of the passage 16 is communicated to an injection part 17.

6 Claims, 5 Drawing Sheets

(A)

(B)

DIAGNOSIS CATHETER FOR INTERSTITIAL CYSTITIS

FIELD OF THE INVENTION

This invention relates to a diagnosis catheter for an interstitial cystitis and more particularly relates to a balloon catheter with electrodes to be used for diagnosis of an interstitial cystitis.

BACKGROUND OF THE INVENTION

A balloon catheter with electrodes is well known and is generally used for diagnosis or treatment of a neurotic cystitis, an acraturesis, or the like. However, there is no example in which the balloon catheter with the electrodes has been used for diagnosis of the interstitial cystitis. Since a conventional balloon catheter with electrodes has exposed hard electrodes, it is not suitable for insertion into a bladder through a urethra.

There is a current perception threshold (CPT) inspection apparatus that has been recently developed to diagnose an abnormality of a peripheral nerve. This inspection apparatus evaluates an amount of a current stimulation at the lowest level that a subject can feel when a feeble alternating current is supplied to a pair of electrodes stuck on a skin of the subject. The CPT inspection apparatus is generally utilized in a measurement of a treatment effect (anesthesia), a measurement of an affected portion (plastic surgery), an evaluation of a diabetic peripheral neuropathy (medicine), a quantitative evaluation of a perceptive nerve (neurology), a diagnosis for distinguishing a disease between an impotence due to a neuropathy and a psychogenetic impotence (urology), an evaluation of an injury and a perception (dentistry), a quantitative measurement of a pharmacodynamics effect (pharmacology), and the like.

The above CPT inspection apparatus is also used in a urology to diagnose a urinary organ outside a body of the subject. However, the CPT inspection apparatus has not been used for diagnosis of the interstitial cystitis. The interstitial cystitis is a disease that has been found recently. A deterministic diagnosis has not been found yet, although there are many subconscious patients.

The interstitial cystitis is often caused in women in the ages of 20 to 60. The interstitial cystitis often appears as a symptom such as a pain in an upper part of a pubic bone, a thamuria, an urge uresiesthesia, or the like. In a typical mucosa observation, a canker-appears in line-like shapes on a bladder mucosa. Even in a lighter symptom, a spot bleeding appears on a substantially wide area of the bladder mucosa. A general inflammation is a phenomenon that occurs between the time when a tissue is injured and the time when the injured tissue heals. However, the tissue continues to heal in the interstitial cystitis.

Since pathology of the interstitial cystitis has not been resolved yet, a common reference of diagnosis has not been proposed. There are various common methods for diagnosing the interstitial cystitis, such as an endoscopy using a bladder mirror, an observation of an interior in the bladder utilizing an inflation by means of a water pressure, a bladder biopsy in which an inflammatory tissue is removed and inspected outside a body of a subject, and the like. However, any one of the above diagnosis methods is not convenient and precise.

SUMMARY OF THE INVENTION

An initial symptom of the interstitial cystitis is a hypersensitivity in a urethra bladder. There is a method for injecting a K Cl (potassium chloride) into a bladder in one of conventional simple inspection methods. However, this method induces a pain in a subject and the pain continues after injection of the K Cl. This method is not suitable for a low injury inspection method. The K Cl is a serious matter in the low injury inspection for the interstitial cystitis that can be moderated by filling a C-fiber into the bladder.

An object of the present invention is to provide a diagnosis catheter for an interstitial cystitis that can diagnose the interstitial cystitis simply and precisely and does not cause a pain in a subject.

A diagnosis catheter for an interstitial cystitis in accordance with the present invention is connected to a current perception threshold inspection apparatus to diagnose an interstitial cystitis. The catheter comprises: a catheter body made of a soft flexible material and including a bladder-dwelling distal end section and a diagnosis section adjacent the distal end section at a proximal end side of the body; a core member made of a hard flexible material and inserted into the diagnosis section in the catheter body; an inflatable balloon mounted on an outer periphery around the bladder-dwelling distal end section of the catheter body; a pair of electrodes provided on an outer periphery of the diagnosis section; lead wires inserted into the core member so that first ends of the lead wires are connected to the electrodes and second ends of the lead wires are drawn out of a proximal end of the catheter body to be connected to the current perception threshold inspection apparatus; and a fluid supply passage provided in the catheter body so that an end of the passage is communicated to the balloon and a proximal end of the passage is communicated to an injection part.

The electrodes may be separated away from each other in a diametrical direction of the catheter body or in an axial direction of the catheter body. Otherwise, the electrodes may be ring-like electrodes that extend continuously in a peripheral direction of the catheter body and separated away form each other in an axial direction of the body.

The balloon attached to the bladder-dwelling distal end section is retained in the bladder after being inflated and a current is supplied to the pair of electrodes provided on the outer periphery of the catheter body. The catheter is formed into a soft structure since a part of the catheter from the distal end to a portion supporting the balloon is inserted into the urethra. The other part of the catheter from a portion supporting the electrodes to the proximal end is formed into a dual structure in order to prevent connecting portions between the electrodes and the lead wires and the lead wires themselves from being broken and in order to positively insert the catheter into the bladder. A conventional stylet for a catheter cannot be used since the lead wires pass through a lumen in the core member.

Also, preferably, the electrodes to be used are made of a flexible material that gives less stimulation to the mucosa.

PREFERRED EMBODIMENTS OF THE INVENTION

Figure 1:
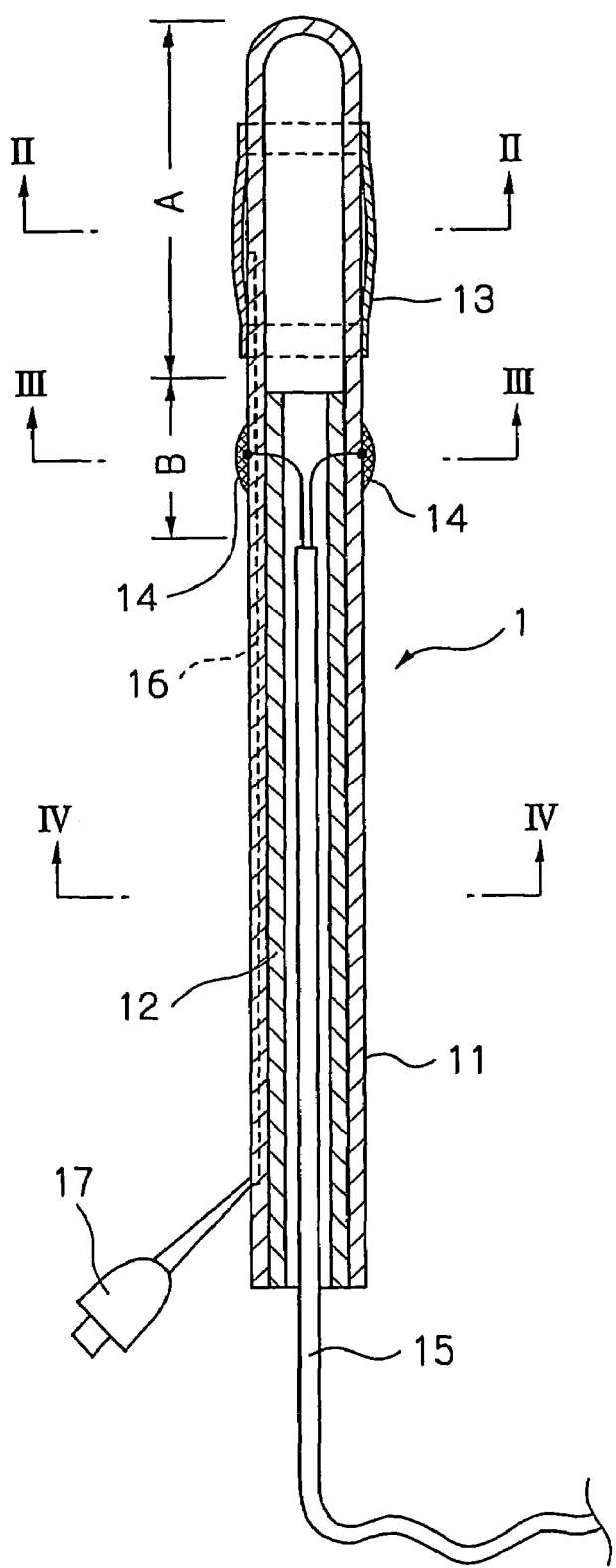
FIG. 1 is a schematic longitudinal sectional view of an embodiment of a diagnosis catheter for an interstitial cystitis in accordance with the present invention.
Figure 2:
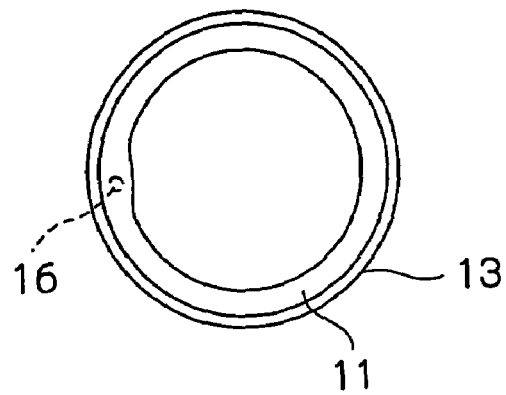
FIG. 2 is a cross sectional view of the catheter taken along line II-II in FIG. 1.
Figure 3:
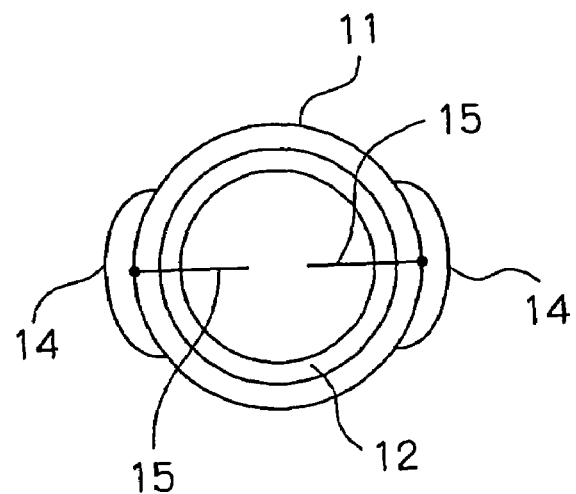
FIG. 3 is a cross sectional view of the catheter taken along line III-III in FIG. 1.
Figure 4:
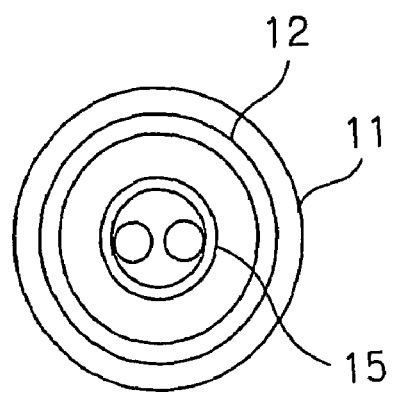
FIG. 4 is a cross sectional view of the catheter taken along line IV-IV in FIG. 1.

Referring now to FIGS. 1 to 5, an embodiment of a diagnosis catheter 1 for an interstitial cystitis in accordance with the present invention will be described below. As shown in FIG. 1, the diagnosis catheter 1 for the interstitial cystitis in accordance with the present invention is connected to a current perception threshold inspection apparatus 4 (CPT inspection apparatus) shown in FIG. 6 and is used to diagnose the interstitial cystitis.

The diagnosis catheter 1 for the interstitial cystitis in accordance with the present invention includes mainly a catheter body 11, a core member 12, an inflatable balloon 13, a pair of electrodes 14, lead wires 15, and a fluid supply passage 16.

The catheter body 11 is made of a soft flexible material (for example, silicone rubber) and includes a bladder-dwelling distal end section A and a diagnosis section B adjacent the distal end section A at a proximal end side of the body 11. The core member 12 is made of a hard flexible material (for example, TEFLON (trade name)) and is inserted into the diagnosis section B in the catheter body 11. The inflatable balloon 13 is mounted on an outer periphery around the bladder-dwelling distal end section A of the catheter body 11.

The pair of electrodes 14 are provided on an outer periphery of the diagnosis section B. The lead wires 15 are inserted into the core member 12 so that first ends of the lead wires 15 are connected to the electrodes 14 and second ends of the lead wires 15 are drawn out of a proximal end of the catheter body 11 to be connected to the current perception threshold inspection apparatus 4.

The fluid supply passage 16 is provided in the catheter body 11 so that an end of the passage 16 is communicated to the balloon 13 and a proximal end of the passage 16 is communicated to an injection part 17. A fluid (for example, air, water, or the like) is supplied through the injection part 17 to the balloon 13 to inflate the balloon 13.

Figure 5:
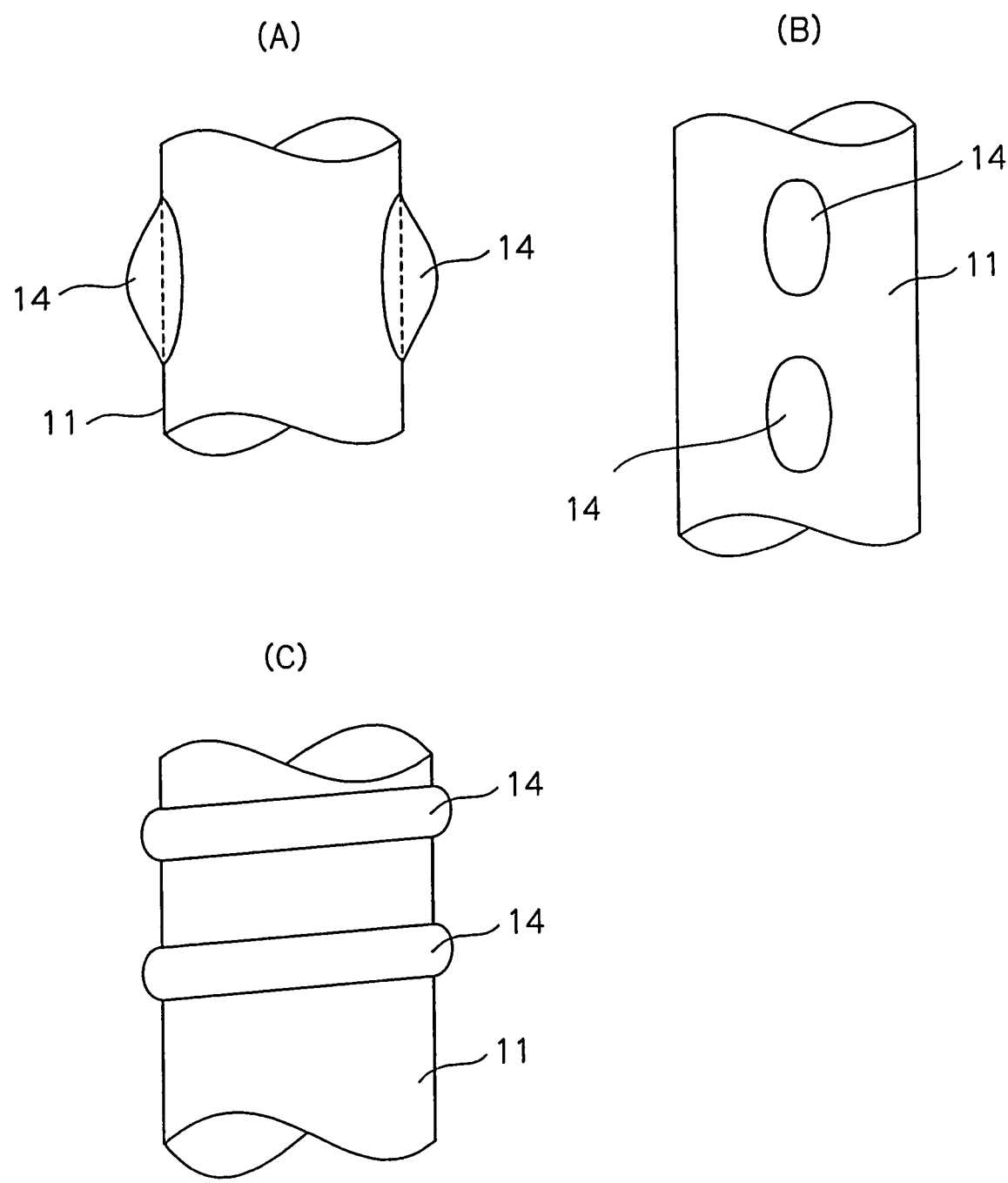
FIGS. 5(A) to 5(C) are partial plan views of a portion of the catheter in accordance with the present invention, illustrating various modifications of electrodes of the catheter.

The electrodes 14, as shown in FIG. 5, may be separated away from each other in a diametrical direction of the catheter body (FIG. 5(A)) or in an axial direction of the catheter body (FIG. 5(B)). Otherwise, the electrodes 14 may be ring-like electrodes that extend continuously in a peripheral direction of the catheter body 11 and separated away form each other in an axial direction of the body 11 (FIG. 5(C)).

EXAMPLE

Figure 6:
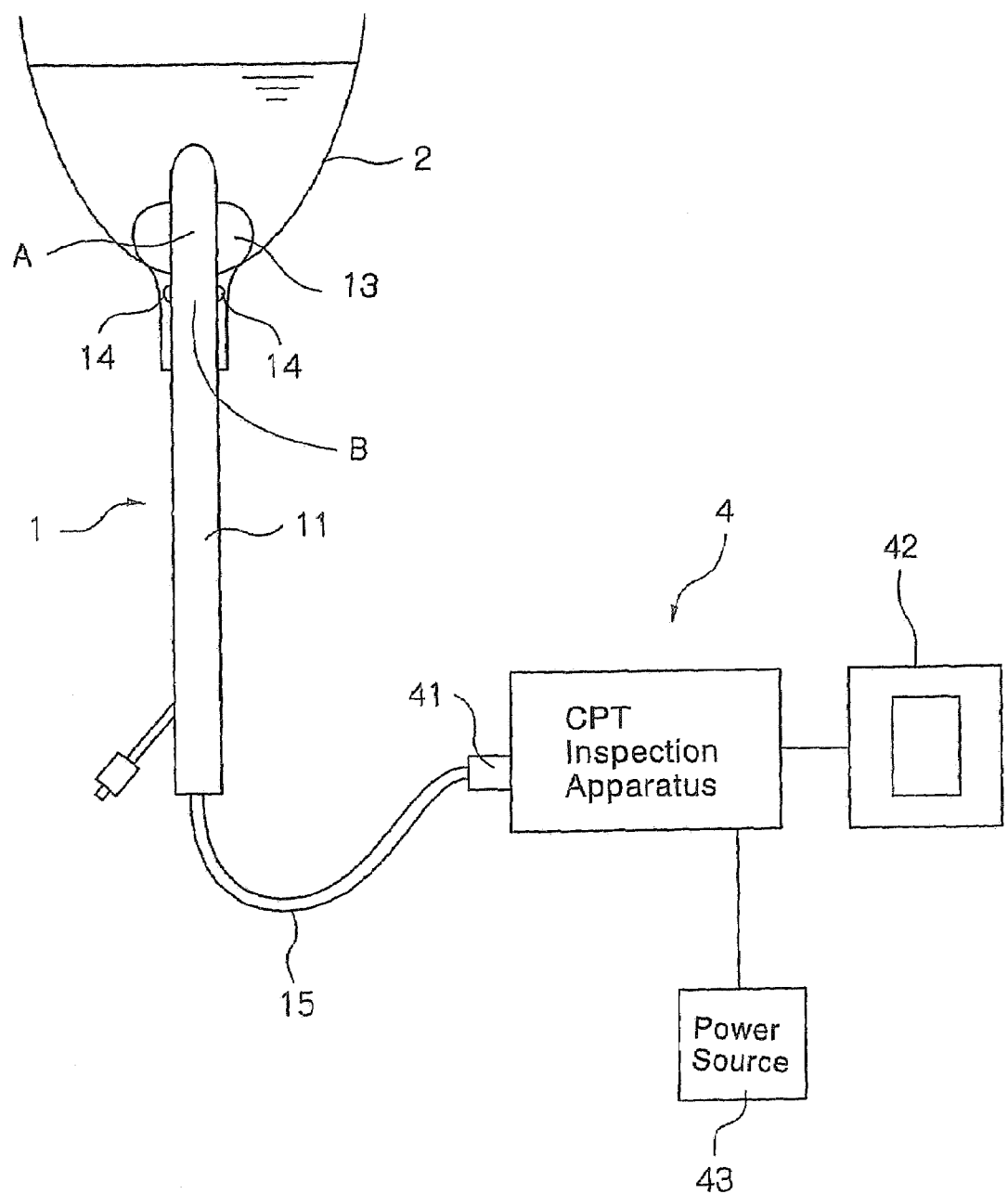
FIG. 6 is an explanatory view of an example in which the catheter of the present invention is used for diagnosis of an interstitial cystitis.
Figure 7:
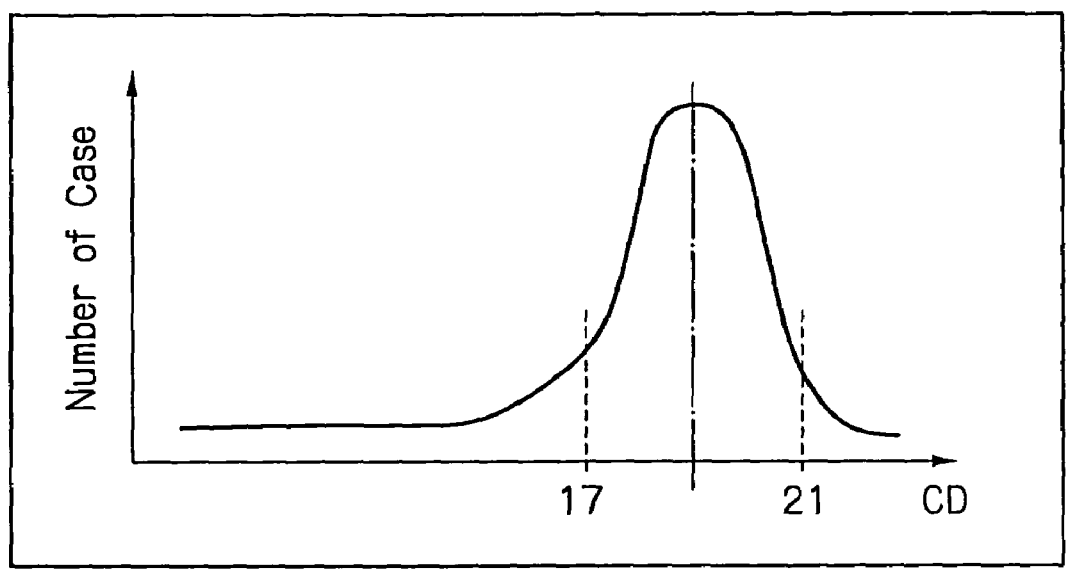
FIGS. 7(A) and 7(B) are graphs illustrating a diagnosis result of each interstitial cystitis indicated on a display of a current perception threshold inspection apparatus, FIG. 7(A) illustrating a normal value, and FIG. 7(B) illustrating an abnormal value.
Figure 7:
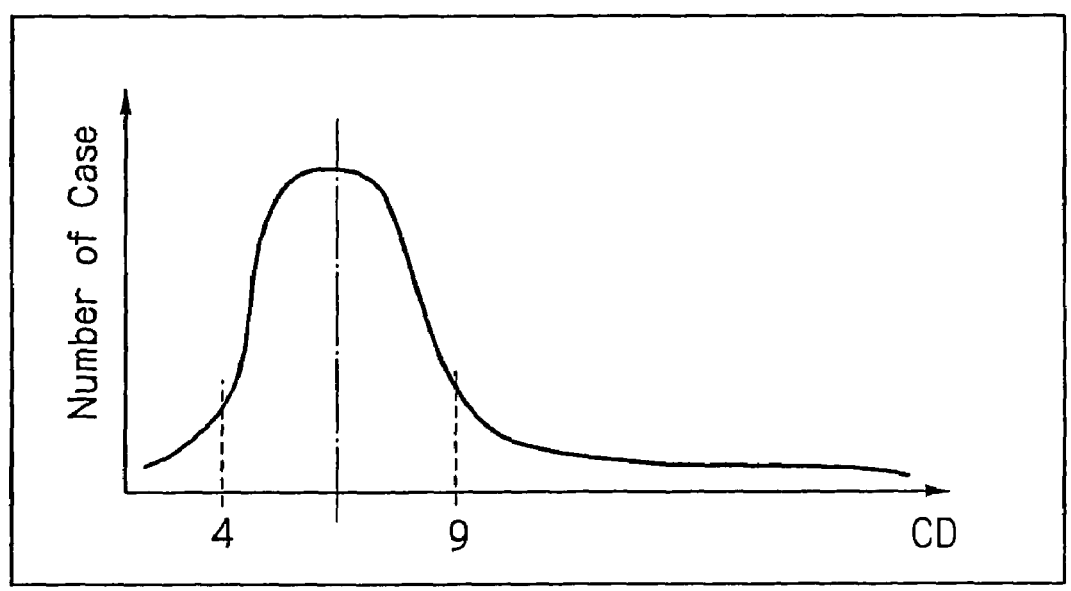

Referring to FIGS. 6 and 7, an example of diagnosis of the interstitial cystitis utilizing the catheter 1 of the present invention will be explained below.

As shown in FIG. 6, the catheter 1 is inserted into a bladder 2 in a patient. The balloon 13 of the catheter 1 is inflated to retain the bladder-dwelling distal end section A of the catheter body 11. At this time, the diagnosis section B of the catheter body 11 is disposed on an affected area near an inlet port of the bladder 2. The lead wires 15 extending from the proximal end of the catheter 1 are connected to an input terminal 41 of the current perception threshold inspection apparatus 4. A power source 43 and a display 42 are connected to the apparatus 4.

A feeble alternating current with a given frequency (5 to 2000 Hz) is supplied from the current perception threshold inspection apparatus 4 to the lead wires 15 of the catheter 1. The current flows through the electrodes 14 into the affected area in the bladder 2. The display 42 indicates a current level at the time when the patient feels the current flow. FIG. 7 shows an example of an indicating result of the current flow feeling-level. FIG. 7(A) shows a normal value while FIG. 7(B) shows an abnormal value.

POSSIBILITY OF UTILIZATION IN AN INDUSTRIAL FIELD

According to the present invention, it is possible to simply and precisely diagnose an interstitial cystitis by using a catheter having a simple and inexpensive structure. The catheter does not cause a pain in a subject during inspection. The catheter of the present invention will be useful for a diagnosis of an irritable bowel syndrome.

The invention claimed is:

1. A diagnosis catheter for an interstitial cystitis wherein a catheter is connected to a current perception threshold inspection apparatus to diagnose an interstitial cystitis, wherein the current perception threshold inspection apparatus indicates a current level at the time when a patient feels the current flow, the diagnosis catheter comprising:

a catheter body made of a soft flexible material and including a bladder-dwelling distal end section and a diagnosis section adjacent said distal end section at a proximal end side of said body;

a core member made of a hard flexible material and inserted into said diagnosis section in said catheter body;

an inflatable balloon mounted on an outer periphery around said bladder-dwelling distal end section of said catheter body;

a pair of electrodes provided on an outer periphery of said diagnosis section, wherein the electrodes supply electric current flow at a level such that it can be felt by the patient;

lead wires inserted into said core member so that first ends of said lead wires are connected to said electrodes and second ends of said lead wires are drawn out of a proximal end of said catheter body to be connected to said current perception threshold inspection apparatus; and a fluid supply passage provided in said catheter body so that an end of said passage is communicated to said balloon and a proximal end of said passage is communicated to an injection part.

2. A diagnosis catheter for an interstitial cystitis according to claim 1, wherein said electrodes are separated away from each other in a diametrical direction of said catheter body.

3. A diagnosis catheter for an interstitial cystitis according to claim 1, wherein said electrodes are separated away from each other in an axial direction of said catheter body.

4. A diagnosis catheter for an interstitial cystitis according to claim 1, wherein said electrodes are ring-like electrodes that extend continuously in a peripheral direction of said catheter body and separated away form each other in an axial direction of said body.

5. A diagnosis system comprising:
a diagnosis catheter comprising:
a catheter body made of a soft flexible material and including a bladder-dwelling distal end section and a diagnosis section adjacent said distal end section at a proximal end side of said body;
a core member made of a hard flexible material and inserted into said diagnosis section in said catheter body;
an inflatable balloon mounted on an outer periphery around said bladder-dwelling distal end section of said catheter body;
a pair of electrodes provided on an outer periphery of said diagnosis section, wherein the electrodes supply electric current flow at a level that can be felt by a patient;
lead wires inserted into said core member so that first ends of said lead wires are connected to said electrodes and second ends of said lead wires are drawn out of a proximal end of said catheter body to be connected to said current perception threshold inspection apparatus, wherein the current perception threshold inspection apparatus indicates a current level at the time when the patient feels the current flow; and
a fluid supply passage provided in said catheter body so that an end of said passage is communicated to said balloon and a proximal end of said passage is communicated to an injection part, wherein
said current perception threshold inspection apparatus connected to said diagnosis catheter;
a display connected to said current perception threshold inspection apparatus; and
a power source connected to said current perception threshold inspection apparatus.

6. A diagnosis system as recited in claim 5, wherein:
said electrodes are separated away from each other in a diametrical direction of said catheter body, and
said current perception threshold inspection apparatus is connected to said diagnosis catheter; said system further comprising:
a display connected to said current perception threshold inspection apparatus; and
a power source connected to said current perception threshold inspection apparatus.

* * * * *